United States Patent [19]

Fünfschilling

[11] Patent Number: 5,543,531

[45] Date of Patent: Aug. 6, 1996

[54] THIOPHEN COMPOUNDS AND THEIR PREPARATION

[75] Inventor: Peter Fünfschilling, Allschwil, Switzerland

[73] Assignee: Sandoz Ltd., Basle, Switzerland

[21] Appl. No.: 870,151

[22] Filed: Apr. 8, 1992

Related U.S. Application Data

[63] Continuation of Ser. No. 768,092, Sep. 30, 1991, abandoned, which is a continuation of Ser. No. 575,537, Aug. 28, 1990, abandoned, which is a continuation of Ser. No. 336,356, Feb. 15, 1989, abandoned.

[30] Foreign Application Priority Data

Jun. 16, 1987 [GB] United Kingdom ............... 8714005

[51] Int. Cl.$^6$ ............................................. C07D 333/32
[52] U.S. Cl. ............................................. 549/62
[58] Field of Search ............................................. 549/62

[56] References Cited

U.S. PATENT DOCUMENTS

4,645,842  2/1987  Corey ........................................ 549/62

OTHER PUBLICATIONS

Hornefeldt Chem Abst vol. 63 16287D (1965).

*Primary Examiner*—Alan Siegel
*Attorney, Agent, or Firm*—Lynn Marcus-Wyner; Allen E. Norris

[57] ABSTRACT

Processes for the preparation of N-(2,4-dimethylthien-3-yl)-N-(1-methoxyprop-2-yl)-chloroacetamide and of intermediates thereof, and novel intermediates useful for the preparation of N-(2,4-dimethylthien-3-yl)-N-(1-methoxyprop-2-yl)-chloroacetamide.

2 Claims, No Drawings

THIOPHEN COMPOUNDS AND THEIR PREPARATION

This is a continuation of application Ser. No. 07/768,092, filed Sep. 30, 1991 now abandoned, which is a continuation of application Ser. No. 07/575,537, filed Aug. 28, 1990, now abandoned, which is a continuation of application Ser. No. 07/336,356, filed Feb. 15, 1989, now abandoned.

The present invention relates to novel processes for the preparation of N-(2,4-dimethylthien-3-yl)-N-(1-methoxyprop-2-yl)-chloroacetamide (hereinafter designated thienyl-chloroacetamide) and of intermediates thereof and to novel intermediates useful for the preparation of the thienylchloroacetamide.

UK 2 114 566 discloses the thienyl-chloroacetamide, herbicidal properties of said compound and processes for preparing it. The processes in UK 2 114 566 have various disadvantages. EPA 210320 discloses an improved process of preparing the thienyl-chloracetamide employing better available starting materials. Said process has the ecological disadvantage that it involves the use of thionylchloride as oxidation agent.

The present invention provides novel advantageous processes for the preparation of the thienyl-chloroacetamide and of intermediates therefore. The novel processes allow the preparation of thienyl-chloroacetamide in high yields and are ecologically acceptable. The processes involve also novel intermediates.

Accordingly, the invention provides 2,4-dimethyl-2,3-dihydro-thiophen- 3-one of formula Ia, which may also exist in its tautomeric enol-form of formula Ib

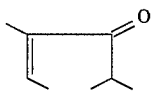   Ia

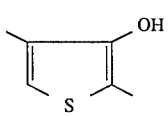   Ib or salts thereof. The compound of formula Ib may be converted to its salts in a manner known per se or vice versa. The compound of formula Ia or Ib (hereinafter designated formula I) is obtained by a) treating a compound of formula III

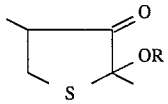   III wherein R is H, the aliphatic hydrocarbyl moiety of an alkanol, or $C_{2-4}$alkanoyl, with an organic carboxylic acid in the presence of an amine, or b) treating a compound of formula IIIb

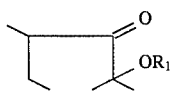   IIIb wherein $R_1$ is the aliphatic hydrocarbyl moiety of an alkanol, with NaOH, and converting where desired the thus obtained Na salt of the compound of formula Ib into its free keto/enol form.

Process a) is conveniently effected by treating a solution of the compound of formula III with an alkanecarboxylic acid such as glacial acetic acid, propionic acid and the like. The reaction is effected in the presence of an amine, e.g. a tertiary amine such as triethylamine or a secondary or primary amine such as 1-methoxy-2-propylamine (hereinafter referred to as methoxyisopropylamine). Suitable solvents are solvents which are inert under the reaction conditions, e.g. an hydrocarbon such as n-hexane, toluene, xylene, a chlorinated hydrocarbon such as 1,2-dichloroethane, or mixtures thereof. The compound of formula III may also be and is conveniently prepared in situ and reacted further without isolation. More details on this aspect of the invention will be given below. A suitable reaction temperature for process a) lies in the range of 20° C.–80° C., e.g. at 60° C.–75° C. The reaction is preferably effected at pH 5 to 12, more preferably at pH 5–8.

Process b) is conveniently effected in a solvent which is inert under the reaction conditions, i.e. an alkanol such as methanol. A suitable reaction temperature for process b) lies in the range of 20° C. to 80° C., e.g. at 60° C. The reaction runs smoothly and there is accordingly no need to work at higher temperature. The pH is preferably in the range of 5–12.

Like in process a), the compound of formula III may be prepared in situ and reacted further without isolation (see below).

The compound of formula III, where R is hydrogen may be readily obtained from 4-methyl-4-pentene-2,3-dione of formula IV

   IV by treatment with $H_2S$ in the presence of a base (process c).

Process c) is essentially a Michael addition and can be effected under the conditions known for such reaction. The reaction is carried out in the presence of an anorganic or organic base, e.g. an alkalimetal hydroxide such as NaOH, or a primary, secondary or tertiary amine, such as methoxy-iso propylamine, triethylamine and the like. The reaction requires the presence of only catalytical amounts of base.

The reaction of process c) proceeds already at temperature of –40° C. A suitable reaction temperature is for example from 0° to 20° C., e.g. from 0° to 5° C.

The compound of formula IV, $H_2S$ and the base may be and preferably are employed in equimolar amounts.

Process c) is conveniently effected in a solvent which is inert under the reaction conditions, e.g. in a hydrocarbon such as hexane, toluene, xylene, an alkanol such as methanol, a chlorinated hydrocarbon such as 1,2-dichloroethane or mixtures thereof. The $H_2S$ may be introduced in gas form into the reaction mixture.

It is however also possible to add the compound of formula IV to a mixture of $H_2S$ and a base in a solvent which is inert under the reaction conditions.

After the reaction is complete, which can be established by known methods, e.g. chromatographically, the compound of formula III may be converted without further isolation to the compound of formula I, employing process a). The compound of formula III may, of course, also be isolated and then reacted in the next step.

Compounds of formula III are obtained by oxidation of the compound of formula V

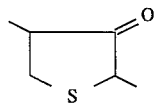   V with an aqueous solution of a peroxide, optionally in the presence of an alkanol or a $C_{2-4}$ carboxylic acid (process d).

Where process d) is carried out in the absence of an alkanol or a carboxylic acid, the compound of formula III wherein R is H is obtained. (Compound of formula IIIa).

Where process d) is carried out in the presence of an alkanol, a compound of formula III wherein R is the aliphatic hydrocarbyl moiety of an alkanol, is obtained (Compounds of formula IIIb). Examples of alkanols suitable for use in process d) are methanol, ethanol, isopropanol, hexanol; they allow the preparation of compounds of formula IIIb, wherein $R_1$ is $C_{1-6}$ alkyl. $R_1$ is particularly $C_{1-4}$ alkyl, most preferably methyl.

Where process d) is carried out in the presence of a $C_{2-4}$ carboxylic acid, a compound of formula III is obtained wherein R is $C_{2-4}$ alkanoyl (Compounds of formula IIIc). Where R is $C_{2-4}$ alkanoyl it is preferably acetyl.

An example of an aqueous peroxide suitable for use in process d) is aqueous $H_2O_2$, e.g. a 35% $H_2O_2$ solution. Reaction d) is exothermic. The reaction temperature lies conveniently between 40° C. and 80° C., e.g. at 60° C. to 65° C.

Compounds of formula IIIb are also obtained by treating the compound of formula IIIa with an aliphatic alkanol in the presence of a strong acid (process e).

In process e) the acid needs only to be present in catalytical amounts. Suitable acids are for example protonating acids such as HCl. Examples of suitable alkanols ($R_1OH$) are methanol, ethanol, isopropanol, hexanol etc. A suitable procedure is for example to employ the alkanol ($R_1OH$) as solvent.

A suitable reaction temperature is from 20° C. to 80° C., e.g. 40° C. to 60° C.

The compounds of formula IV and V are known. A suitable process for the preparation of the compound of formula V is disclosed in EPA 210320.

A process for the preparation of the compound of formula IV is disclosed by A. Shabanov et al. in Dokl. Akad. Nauk Azerb. SSR 27(6), 42–46 (1971).

It has been found that the compound of formula IV is, in general, partly obtained in its dimeric form of formula VI

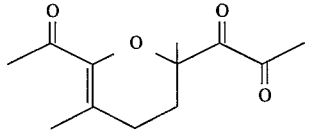

VI

The proportion of dimeric form obtained will depend on the reaction conditions employed for the preparation of the compound of formula VI. It has also been observed that the compound of formula IV dimerizes in undiluted form at room temperature (though said compound can be stored in a hydrocarbon such as hexane or toluene).

It has now been found that the monomeric compound, of formula IV may be obtained by pyrolysis of the compound of formula VI (process f), and this in high yields.

A suitable reaction temperature for process f) is between 400° C. and 600° C. at a pressure of 0.01 to 100 Torr, e.g. at 4 to 8 Torr. The compound of formula VI may be distilled under the aforementioned conditions, e.g. in a quartz tube.

The compound of formula VI is conveniently obtained by elimination of HBr from the compound of formula VII

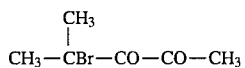

VII in the presence of an acid binding agent (process g).

Said process g) may be effected under the conditions known for the preparation of olefines from halogenated aliphatic ketones. The reaction is conveniently carried out in a solvent which is inert under the reaction condition for example an aliphatic or aromatic hydrocarbon such as hexane or xylene. The reaction temperature is preferably above room temperature, e.g. in the range of 100° C. to 130° C. when employing xylene as a solvent. Examples of suitable acid binding agents are tertiary alkylamines, such as $N(nC_4H_9)_3$. As indicated earlier, part of the compound of formula IV will directly dimerize under the reaction conditions to the compound of formula VI; the latter compound may then be converted to the compound of formula IV by pyrolysis.

The reaction of the compound of formula I with 1-methoxy-2-propylamine allows the production of the N-(1-methoxyprop-2-yl)-2,4-dimethylaminothiophene in high yields (process h).

Such process h) is conveniently effected in an autoclave. 1-Methoxy-2-propylamine may thereby serve as solvent. The reaction is advantageously carried out in the presence of an acid such as hydrochloric acid. The reaction temperature is preferably above 100° C., e.g. between 150° C. and 220° C.

Reaction of N-(1-methoxyprop-2-yl)-2,4-dimethylaminothiophene with chloroacetylchloride, under the conditions analogous to those of the process of EPA 210320, yield then the desired thienyl-chloroacetamide.

The invention may be illustrated by the following examples in which temperatures are in Centigrades.

EXAMPLE 1

2,4-Dimethyl-2,3-dihydrothiophen-3-one and 2,4-dimethyl-3-hydroxythiophene a. 2,4-Dimethyl-2-hydroxy-tetrahydro-thiophen-3-one Into a solution of 224 mg (0.20 mmol) of 4-methyl-4-pentene-2,3-dione and 202 mg (0.20 mmol) of triethylamine in 5 ml of n-hexane and 3 ml of 1,2-dichloroethane are introduced within 1 hour and at 0°–5° internal temperature, 70 mg of $H_2S$ gas. After said hour it is no longer possible to determine the starting material (dione) gaschromatographically. The clear solution, comprising 2,4-dimethyl-2-hydroxy-tetrahydrothiophen- 3-one may now, without isolation of the hydroxyketone, be further treated as shown in step b) hereinafter.

The hydroxyketone may also be isolated as follows: the reaction solution is eluated over silica gel employing toluene/ethylacetate 9:1 as eluant, the solvent is evaporated off and the residue distilled in a bulb tube oven. The hydroxyketone (subtitle a) distills at 55° and 0.01 Torr (light yellow oil; according to NMR in the form of a 1:1-cis/trans mixture).

b. Title Compounds (Example 1)

To the reaction solution of Example 1a) are added 0.2 ml acetic acid and the mixture is stirred for 15 hours at 60° (internal temperature). The mixture is concentrated in vacuo and the residue distributed between 5 ml hexane and 5 ml 1N sodium hydroxide. The organic phase is separated and removed.

The aqueous phase is covered with 5 ml hexane and 3 ml saturated ammonium chloride solution are added. The phases are separated and the aqueous phase extracted one more time with 5 ml hexane. The combined organic phases are concentrated in vacuo. The remaining title compound consists according to NMR determination of a tautomeric mixture comprising 60% keto compound and 40% enol compound.

EXAMPLE 2

2,4-Dimethyl-2,3-dihydrothiophen-3-one and 2,4-dimethyl-3-hydroxythiophene a. 2,4-Dimethyl-2-methoxy-tetrahydrothiophen-3-one To a solution of 411 g (3.16 mol) of 2,4-dimethyl-tetrahydro-thiophen-3-one in 3000 ml of methanol are added dropwise, at an internal temperature of 63°–65° and over a period of one hour, 256.4 g (2.70 mol) of 35.8% hydrogen peroxide.

The reaction is exothermic; from time to time it is necessary to remove the heating bath. After the addition is completed the reaction mixture is stirred for another 2 hours at the internal temperature of 63°–65°. The reaction mixture comprises, according to gas chromatographical determination—besides some 2,4-dimethyl-2-hydroxy-tetrahydrothiophene-3-one mainly 2,4-dimethyl-2-methoxy-tetrahydrothiophen-3-one.

b. 2,4-Dimethyl-2,3-dihydrothiophen-3-one and 2,4-dimethyl-3-hydroxythiopene

The reaction mixture of Example 2a is cooled to 60° and then 240 ml of an aqueous 30% (2,43 mol) sodium hydroxide solution are added. After 15 minutes stirring at 60° the reaction mixture has turned violet. It contains according to the gas chromatogram no more 2,4-dimethyl-2 -methoxy-tetrahydrothiophen-3-one.

The reaction is then concentrated in vacuo. The residue is diluted with 1500 ml of water and non-phenolic compounds are removed by extraction with cyclohexane (3×300 ml). The aqueous phase is covered with 300 ml cyclohexane and, at an internal temperature of 20°–25°, adjusted at pH=9.0 by dropwise addition of 205 ml (1.97 mol) of conc. hydrochloric acid. The phases are separated, and the aqueous phase is extracted again with cyclohexane (4×300 ml). The combined organic phases are concentrated in vacuo and the residue is distilled under low absolute pressure: the main fraction distills over at 53°–60° and 0.02 Torr, as a light yellow oil, consisting according to NMR of a tautomeric mixture of the title compound comprising ca. 60% of the keto compound and 40% of the enol compound.

EXAMPLE 3

2,4-Dimethyl-2,3-dihydrothiophene-3-one and 2,4-dimethyl-3 -hydroxythiophene a. 2,4-Dimethyl-2-methoxy-tetrahydrothiophen-3-one To a solution of 261 g (2.0 mol) of 2,4-dimethyl-tetrahydrothiophen-3one and 6 g of acetic acid in 600 ml of methanol are added dropwise, at an internal temperature of 20°–25° (external cooling with ice/water) over a period of 3 hours 207 g (2.1 mol) of 34.5% hydrogen peroxide. The reaction mixture is then stirred over night at 20°–25°. According to gas chromatographical determination the reaction mixture comprises—beside some 2,4-dimethyl-2-hydroxy-tetrahydrothiophene-3-one (compound IIIa)—mainly 2,4-dimethyl-2-methoxy-tetrahydrothiophene-3-one.

b. 2,4-Dimethyl-2,3-dihydrothiophen-3-one and 2,4-dimethyl-3-hydroxythiophene

By adding 5 ml of 30% NaOH the pH of the reaction mixture is adjusted from 2.5 to 6.2. The methanol is distilled off at ca. 900 mbar (internal temperature=74°, duration=3 hours). During this distillation both compound IIIa and compound IIIb ($R_1$=$CH_3$) are transformed to the keto/enol mixture Ia and Ib.

To the mixture (now two phases) are added 500 ml of toluene and 100 ml of water. After separation the organic layer is washed with 100 ml of water and the combined aqueous phases are extracted with 100 ml of toluene. The toluene is removed by distillation. 269 g of a dark yellow oil (269 g) are obtained which is distilled at 30 mmHg, b.p.= 110°–115°. Yield=214 g. Purity (according to gas chromatographical determination) is 95.2% by weight.

EXAMPLE 4

N-(1-methoxyprop-2-yl)-2,4-dimethyl-3-aminothiophene

In a 200 ml autoclave are heated, at 190°, with stirring 12.8 g (0.10 mol) of the 60:40 mixture of 2,4-dimethyl-2,3-dihydrothiophen-3-one and 2,4-dimethyl-3-hydroxythiopene, 100 ml of 1-methoxy-2-propylamine and 8.5 ml conc. hydrochloric acid. The pressure rises thereby to maximum 9 bar.

The reaction mixture is worked up by adding 15 ml of 30% sodium hydroxide solution and removal of the excess of 1-methoxy-2-propylamine in vacuo.

To the evaporation residue are added 100 ml of water and 100 ml of cyclohexane and the phases separated in a separating funnel. The aqueous phase is extracted again with cyclohexane (3×50 ml).

To the combined organic phases are added 50 ml of water. Then 15 ml of conc. hydrochloric acid are added to adjust the organic solution at pH=1. The phases are separated and the organic phase washed with water (2×50 ml.

The combined aqueous phases are covered with 100 ml of cyclohexane and adjusted at pH=13 with 22 ml of 30% sodium hydroxide solution. After separation with a separating funnel the aqueous phases are again extracted with cyclohexane (2×50 ml). The combined organic phases are completely concentrated to give the title compound having a gas chromatographical purity of 96.3%.

EXAMPLE 5

4-Methyl-4-pentene-2,3-dione 10.0 g (0.089 mol) of 6-acetyl-2,5-dimethyl-2-(1,2-dioxo-propyl)-2H- 3,4-dihydropyran is distilled at 6 Torr through a quartz tube which was preheated at 500° to give the title compound.

EXAMPLE 6

6-Acetyl-2,5-dimethyl-2-(1,2-dioxo-propyl)-2H-3,3-dihydropyran (Compound of formula VI—process f)

A mixture of 60.0 g (0.31 mol) of 4-bromo-4-methyl-pentane-2,3-dione, and 0.1 g hydroquinone in 300 ml of tri-(n-butyl)amine and 1200 ml of xylene is stirred for 10 hours at 130° internal temperature. The reaction mixture contains then, according to chromatographical determination, a mixture of 10% of 4-methyl-4-pentene-2,3-dione and 90% of the title compound.

100 ml of conc. hydrochloric acid are then added while cooling the reaction mixture with ice. The phases are separated. The organic phase is washed with water (3×250 ml) and completely concentrated in vacuo. The residue is distilled to give the title compound (b.p. 102°–106° at 6 Torr) as a light yellow oil.

I claim:

1. A process of preparing 2,4-dimethyl-2,3-dihydrothiophen- 3-one of formula Ia/Ib

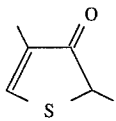
Ia
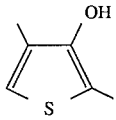
Ib
comprising treating a compound of formula III
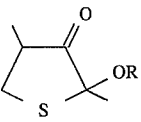
III
wherein R is H, the aliphatic hydrocarbyl moiety of an alkanol or $C_{2-4}$alkanoyl, with an alkane carboxylic acid in the presence of an amine.
2. The compounds of formulae Ia and Ib, stated in claim 1.
* * * * *